(12) United States Patent
Huang et al.

(10) Patent No.: US 10,295,487 B2
(45) Date of Patent: May 21, 2019

(54) IN SITU NMR PARAMETER MONITORING SYSTEMS AND METHODS FOR MEASURING PH AND TEMPERATURE

(71) Applicant: The Curators of the University of Missouri, Columbia, MO (US)

(72) Inventors: Ming Huang, Rolla, MO (US); Lingyu Chi, Rolla, MO (US); Rex E. Gerald, II, Rolla, MO (US); Jie Huang, Rolla, MO (US); Annalise R. Pfaff, Rolla, MO (US); Klaus Woelk, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 543 days.

(21) Appl. No.: 14/884,686

(22) Filed: Oct. 15, 2015

(65) Prior Publication Data

US 2016/0109390 A1     Apr. 21, 2016

Related U.S. Application Data

(60) Provisional application No. 62/137,057, filed on Mar. 22, 2015, provisional application No. 62/122,235, filed on Oct. 15, 2014.

(51) Int. Cl.
*G01N 24/08* (2006.01)
*G01R 33/00* (2006.01)
(Continued)

(52) U.S. Cl.
CPC .............. *G01N 24/08* (2013.01); *G01K 7/36* (2013.01); *G01R 33/0052* (2013.01);
(Continued)

(58) Field of Classification Search
CPC ...... G01R 33/28; G01R 33/30; G01R 33/307; G01R 33/46; G01R 33/465;
(Continued)

(56) References Cited

U.S. PATENT DOCUMENTS 3,630,191 A   12/1971   Gilford
4,510,450 A    4/1985   Brown
(Continued)

OTHER PUBLICATIONS

International Search Report with Written Opinion dated Feb. 3, 2017 in International Patent Application No. PCT/US16/61551, 12 pages.

(Continued)

*Primary Examiner* — Huy Q Phan
*Assistant Examiner* — Dustin R Dickinson
(74) *Attorney, Agent, or Firm* — Shook, Hardy & Bacon L.L.P.

(57) ABSTRACT

Devices and methods are provided for measuring temperatures and pHs of a sample in situ using NMR spectroscopy, and for sealing one or more ends of a capillary tube after a reference material has been added to the capillary tube, which is used in an in situ NMR temperature measurement device. A method for measuring a pH of a sample in situ using NMR spectroscopy includes providing an in situ NMR pH measurement device. This device includes a sample housing member configured to house a target sample, at least one pH sensor configured to exhibit an NMR spectral change due to a change in pH value of the target sample, and a pH sensor containment member configured to house the at least one pH sensor. The target sample is added to the sample housing member. NMR spectra are obtained to then determine the pH of the target sample.

10 Claims, 14 Drawing Sheets

(51) Int. Cl.
*G01K 7/36* (2006.01)
*G01R 33/48* (2006.01)
*G01R 33/30* (2006.01)
*G01R 33/31* (2006.01)

(52) U.S. Cl.
CPC ........ *G01R 33/4804* (2013.01); *G01R 33/307* (2013.01); *G01R 33/31* (2013.01)

(58) Field of Classification Search
CPC ............ G01R 33/4804; G01R 33/0052; G01R 33/4828; G01K 13/00
See application file for complete search history.

(56) References Cited

U.S. PATENT DOCUMENTS

| | | | |
|---|---|---|---|
| 5,125,408 A * | 6/1992 | Basser | A61B 5/03 600/410 |
| 6,054,857 A | 4/2000 | Doty | |
| 6,596,258 B1 * | 7/2003 | Ballesteros Garcia | A61K 49/06 424/9.3 |
| 7,397,241 B2 | 7/2008 | Gauthausen et al. | |
| 8,367,028 B2 | 2/2013 | Lemon et al. | |
| 2005/0024055 A1 | 2/2005 | Cavaluzzi et al. | |
| 2008/0007262 A1 | 1/2008 | Yamauchi et al. | |
| 2008/0100296 A1 * | 5/2008 | Massin | G01R 33/302 324/321 |
| 2008/0297157 A1 | 12/2008 | Hu et al. | |
| 2010/0156414 A1 | 6/2010 | Sakellariou et al. | |
| 2010/0260665 A1 | 10/2010 | Archer et al. | |
| 2011/0080171 A1 | 4/2011 | Takegoshi et al. | |
| 2014/0005033 A1 | 1/2014 | Ghosh | |
| 2014/0081014 A1 | 3/2014 | Yaghi et al. | |
| 2014/0084928 A1 * | 3/2014 | Gisler | G01R 33/31 324/321 |
| 2016/0051337 A1 * | 2/2016 | Bolan | A61B 19/54 600/424 |
| 2016/0109391 A1 | 4/2016 | Chi et al. | |

OTHER PUBLICATIONS

Non-Final Office Action dated Jan. 19, 2018 in U.S. Appl. No. 14/941,372, 12 pages.
International Preliminary Report on Patentability in PCT Application No. PCT/2016/061551 dated May 24, 2018, 11 pages.
Notice of Allowance dated Jul. 17, 2018 in U.S. Appl. No. 14/941,372, 10 pages.

* cited by examiner

| SPINNING SPEED | DISTANCE | TEMPERATURE |
| --- | --- | --- |
| 14 kHz | 1.39 ppm | 325.78 K |
| 10 kHz | 1.56 ppm | 308.72 K |
| 6 kHz | 1.65 ppm | 299.69 K |
| 2 kHz | 1.7 ppm | 294.67 K |
| 0.5 kHz | 1.72 ppm | 292.67 K |

IN SITU NMR PARAMETER MONITORING SYSTEMS AND METHODS FOR MEASURING PH AND TEMPERATURE

CROSS-REFERENCE TO RELATED APPLICATIONS

This application claims priority to U.S. Provisional Application 62/122,235 filed on Oct. 15, 2014, entitled "In Situ NMR Thermometer," and U.S. Provisional Application 62/137,057 filed on Mar. 22, 2015, entitled "In Situ pH Meter," both of which are incorporated in their entireties herein.

GRANT STATEMENT

None.

FIELD OF THE INVENTION

The present disclosure relates to the field of NMR spectroscopy, and more specifically, to in situ parameter monitoring systems and methods for measuring pH and temperature of NMR samples.

BACKGROUND

Certain conventional electronic devices are commercially available for monitoring intensive properties of NMR samples, such as an electronic pH meter that measures pH values for NMR samples by installing a sensor at the tip of a long, small-diameter rod and positioning such sensor inside an NMR tube, e.g., a 5 mm NMR tube. However, such a conventional device and technique requires the removal of the NMR tube from the NMR probe in order to measure the pH value of the sample. Removing an NMR tube for this purpose is inconvenient when monitoring chemical reactions by in situ NMR spectroscopy, especially when the pH changes unexpectedly and rapidly throughout the course of the reaction. Further, other conventional devices for monitoring NMR samples, such as an NMR temperature probe require placing the device in the probe, making a series of NMR measurements at different probe temperature settings, making a series of corresponding probe temperature measurements with an independent thermocouple or other electronic temperature sensor, removing the device from the probe, and creating a calibration curve. The NMR sample to be analyzed is then placed in the probe, the probe temperature setting is adjusted to a desired value, the NMR sample is allowed to equilibrate to the probe temperature, and the calibration curve is used to predict the temperature of the NMR sample. The explicit assumption is that the calibration curve provides an accurate prediction of the temperature of the NMR sample. It is often the case that the assumption is invalid and that the predicted temperature of the NMR sample is erroneous. Additionally, the conventional device is costly and the procedure for measuring and assigning the temperature of the NMR sample is extensive, tedious, time-consuming, and inherently prone to operator error. Furthermore, the numerical value of temperature that is assigned to the corresponding recorded NMR spectrum lacks incipient integrity and, therefore, can be called into question in legal proceedings.

SUMMARY OF THE INVENTION

A high-level overview of various aspects of the invention is provided here for that reason, to provide an overview of the disclosure and to introduce a selection of concepts that are further described below in the detailed description section below. This summary is not intended to identify key features or essential features of the claimed subject matter, nor is it intended to be used as an aid in isolation to determine the scope of the claimed subject matter.

In an exemplary aspect, a device is provided for in situ pH monitoring of a sample using NMR spectroscopy. The device comprises a sample housing member configured to house a target sample, at least one pH sensor configured to exhibit an NMR spectral change due to a change in pH value of the target sample, and a pH sensor containment member configured to house the at least one pH sensor. The pH sensor containment member is positioned inside at least a portion of the sample housing member. Further, at least a portion of the pH sensor containment member comprises one or more pores, which are configured to allow diffusion of hydronium cations and hydroxide anions.

In another exemplary aspect, a method is provided for measuring a pH of a sample in situ using NMR spectroscopy. The method comprises providing an in situ NMR pH measurement device. The device includes a sample housing member configured to house a target sample, at least one pH sensor configured to exhibit an NMR spectral change due to a change in pH value of the target sample, and a pH sensor containment member configured to house the at least one pH sensor. The method further comprises adding the target sample to the sample housing member, obtaining one or more NMR spectra, and determining the pH of at least a portion of the target sample.

In another exemplary aspect, a device is provided for monitoring a temperature of a sample in situ using NMR spectroscopy. The device comprises an NMR sample tube and at least one capillary tube positioned inside the NMR sample tube. The at least one capillary tube is configured to house a reference material. Further, the device comprises a glass seal at a first end and at a second end of the at least one capillary tube that seals the first end and second end after the reference material has been added.

In another exemplary aspect, a method is provided for measuring a temperature of a sample in situ using NMR spectroscopy. The method comprises providing an in situ NMR temperature measurement device. The device includes an NMR sample tube and at least one capillary tube positioned inside the NMR sample tube. The at least one capillary tube is configured to house a reference material and be sealed once the reference material has been added. The method further comprises adding the target sample to the NMR sample tube, obtaining one or more NMR spectra, and determining the temperature of at least a portion of the target sample based on at least one NMR spectrum of the reference material.

Still yet, in another exemplary aspect, a method is provided for forming a seal at one or both ends of a capillary tube used in an in situ NMR temperature measurement device. The method comprises providing at least one capillary tube used in the in situ NMR temperature measurement device, adding a reference material to at least a portion of the at least one capillary tube, and using an Optical Fiber Arc Fusion Splicer to seal a first end of the at least one capillary tube.

BRIEF DESCRIPTION OF THE DRAWINGS

Illustrative embodiments of the present invention are described in detail below with reference to the attached drawing figures, and wherein.

DETAILED DESCRIPTION

The subject matter of select embodiments of the present invention is described with specificity herein to meet statutory requirements. However, the description itself is not intended to define what we regard as our invention, which is what the claims do.

Overview

Various embodiments described herein include systems and methods for the in situ monitoring of one or more intensive properties of an NMR sample.

In Situ pH Sensor

In one or more embodiments, an in situ pH measuring device can be utilized to measure pH of a sample, or sample environment, in a continuous fashion while observing and/or measuring the NMR spectrum of that sample. The in situ pH measuring device is capable of measuring the pH of an NMR sample in situ that is simple to implement and that encodes and affixes an imprimatur of the measured value of the pH in the NMR spectrum, affording inseparability of the pH and the NMR data and incipient integrity of same.

Figure 1A:
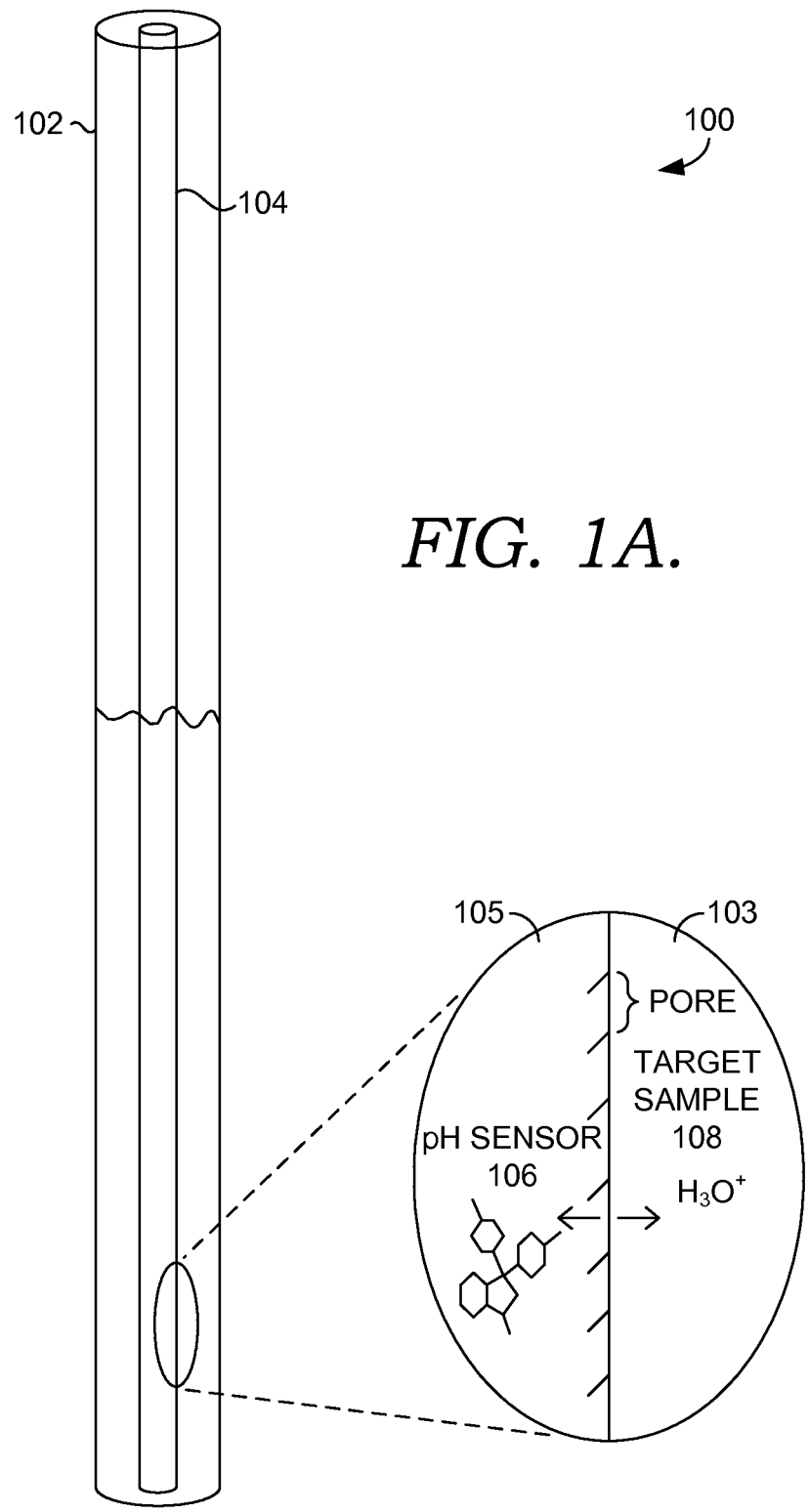
FIG. 1A depicts an in situ pH measuring device, according to one embodiment described herein.
Figure 1B:
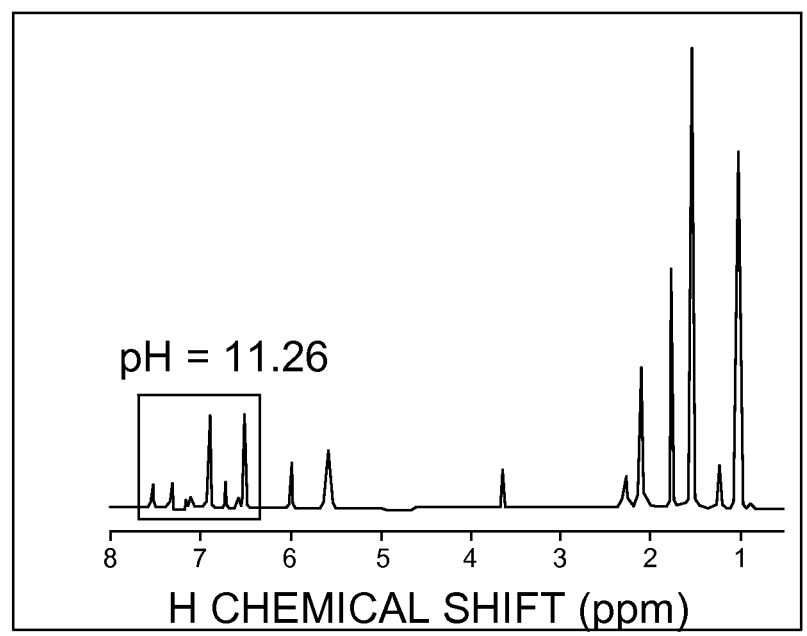
FIG. 1B depicts example NMR spectra that includes the spectral imprint of the in situ pH sensor in the same raw data output NMR spectra of a target sample, according to one embodiment described herein.

One embodiment of an in situ pH measuring device 100 is depicted in FIG. 1A. In embodiments, the in situ pH measuring device 100 can determine pH values of a target sample from a peak or peaks of a spectral pH imprimatur (NMR peaks of a pH sensor molecule which are "embedded" within the NMR spectrum of the sample solution/environment). For example, an example NMR spectra shown in FIG. 1B shows the spectral imprint from the pH sensor molecule (in the box) that is in the same output raw data spectra from the NMR sample.

Unlike a conventional NMR pH meter requiring a user to take out the sample to measure the pH value of a solution contained in a 5-mm NMR tube, the in situ pH measuring device described herein can monitor the pH of a solution while the sample is inside the NMR magnet. Thus, the in situ pH measuring device described herein can be employed to monitor the pH values of a sample solution during the course of a reaction.

The device 100 of FIG. 1 may include a sample housing member 102 and a pH sensor containment member 104 positioned inside of the sample housing member 102. The containment member 104 can be positioned inside of the sample housing member 102 using any techniques known to one skilled in the art, such as one or more annular spacers.

The sample housing member 102 may be any structure suitable for use in NMR and/or MRI that can accommodate a pH sensor containment member. In one embodiment, the sample housing member 102 may be a conventional, commercially available NMR tube, such as a 5 mm outer diameter NMR borosilicate glass tube having a length of about 17 cm. In one or more embodiments, the sample housing member 102 can have an outer diameter of at least about 1 mm, about 2 mm, or about 4 mm, and/or less than about 20 mm, about 15 mm, or about 10 mm.

In embodiments, the sample housing member 102 may define a volume such that a target sample 108 in a preselected sample solution, volume, and/or environment can be positioned in the interior 103 of the sample housing member 102. In the same or alternative embodiments, the pH sensor containment member 104 may define a volume such that a pH sensor 106 can be positioned in the interior 105 of the containment member 104.

In various embodiments, the pH sensor containment member 104 may include various structures and/or materials to provide an interface allowing for the interaction of the pH sensor 106 with hydronium cations and/or hydroxide anions present in the target sample 108 or in the sample housing member 102, but precluding physicochemical interactions between the pH sensor 106 and the target sample 108, e.g., by physically sequestering the pH sensor 106 from direct interaction with the target sample 108. In certain embodiments, the containment member 104 may be a capillary tube with porous walls, e.g., nano-porous walls, having a desired porosity, or a capillary tube with microscopic cracks or fissures. In such embodiments, the desired porosity or the microscopic size or location of the cracks/fissures of the containment member 104 can allow for the bidirectional passage of only small molecules, such as the hydronium cations and/or hydroxide anions. For example, in certain embodiments, the containment member 104 may include pores sized to allow hydronium cations and/or hydroxide anions to diffuse from the sample housing member 102 to the pH sensor containment member 104.

In one or more embodiments, the maximum opening of one or more pores, cracks, and/or fissures present on at least a portion of the containment member 104 to allow for the bidirectional passage of hydronium cations and/or hydroxide anions may be at least about 0.2 Angstroms, at least about 0.3 Angstroms, at least about 0.5 Angstroms, or at least about 1 Angstroms; and/or not more than about 5 Angstroms, not more than about 4 Angstroms, not more than about 3 Angstroms, or not more than about 2 Angstroms. One non-limiting example of a containment member 104 may be a porous VYCOR® capillary tube.

In the one or more embodiments, the containment member 104 may include an interface material, such as any high surface area fiber or thin rod that can tether or entrap pH sensor molecules thereto. In such embodiments, a tethered pH sensor molecule may not be free to diffuse and mix with molecules in the target sample 108 because it is tethered to a fiber; however, such a tethered pH sensor molecule should be chemically inert or innocuous towards the target sample 108, as it may contact the tethered pH sensor molecules.

In certain embodiments, the pH sensor containment member 104 may include a pH sensor 106. In one or more embodiments, the pH sensor 106 exhibits one or more of the following properties: the pH sensor is larger than hydronium ions and/or hydroxide ions so that it may be trapped in a pH sensor containment member 104 while such ions could freely diffuse in and out of the containment member 104; the pH sensor changes structure with a change in pH; the pH sensor can produce NMR signals; the pH sensor can produce NMR signals from nuclei other than the nuclei that produce the NMR spectrum of the target sample; and the pH sensor incorporates nuclei (e.g., $^2$D, $^{12}$C, $^{19}$F, $^{14}$N) into their architecture to make them invisible in the NMR spectrum of the target sample. This last property means that the pH sensor molecule can substitute some of these "dark" nuclei for protons in the pH sensor molecule architecture so that a proton NMR spectrum of the sample under investigation will not include proton signals from the pH sensor molecule.

The pH sensor 106 may include any molecule or ion entity that exhibits a change in particular (or predetermined) concentration as a well-defined function of pH. For example, a change in molecule or ion entity concentration may produce, in direct or other proportion, an NMR and/or MRI detectable change in signal intensity and integral.

In various embodiments, the pH sensor 106 may be of any molecule or ion entity that exhibits a change in the peak volume and/or peak height, or change in chemical shift of one or more nuclear constituents of these entities as a well-defined function of pH. For example, a change in electronic structure of a molecule or ion entity may produce a single-valued NMR and/or MRI detectable change in proton signal chemical shift. In one embodiment, the pH sensor 106 may be unreactive to the target sample 108. In alternative embodiments, the pH sensor may be reactive with the target sample 108.

In one or more embodiments, various molecular and/or ion entities that exhibit an NMR spectral change due to a change in pH may be employed as the pH sensor 106. The changes induced by pH may be in terms of spectral peak volume or chemical shift, whereas the changes may be well-defined/well-calibrated and not interfering with the spectral information of the target sample. In certain embodiments, multiple pH sensors may be employed simultaneously to monitor the pH changes during the course of a reaction. A non-limiting list of commercially available pH sensors with chemical shifts inducible by pH over a certain pH range includes: thymol blue (4-[9-(4-hydroxy-2-methyl-5-propan-2-yl-phenyl)-7,7-dioxo-8-oxa-7λ6-thiabicyclo[4.3.0]nona-1,3,5-trien-9-yl]-5-methyl-2-propan-2-yl-phenol) (pH range of 1.2-2.8); methyl orange (Sodium 4-[(4-dimethylamino)phenyldiazenyl]benzenesulfonate) (pH range of 3.1-4.4); methyl red (2-(N,N-dimethyl-4-aminophenyl) azobenzenecarboxylic acid) (pH range of 4.4-6.2); lithmus (pH range of 5-8); bromothymol blue (4,4'-(1,1-dioxido-3H-2,1-benzoxathiole-3,3-diyl)bis(2-bromo-6-isopropyl-3-methylphenol) (pH range of 6-7.6); BCECF Acid (2',7'-Bis-(2-Carboxyethyl)-5-(and-6)-Carboxyfluorescein) (pH range 6.1-8); thymol phthalein (3,3-bis(4-hydroxy-2-methyl-5-propan-2-ylphenyl)-2-benzofuran-1-one) (pH range of 9.3-10.5); and 4-mercaptobenzoic acid (pH range of 2.5-11). It is appreciated that one skilled in the art would understand how to choose a particular pH sensor and how to prepare it (e.g., prepare a solution comprising a specific concentration of the pH sensor that is applicable to measuring the pH of a sample of interest).

In operation, in certain embodiments, a solution comprising a pH sensor 106 can be placed inside of the pH sensor containment member 104 and placed inside the sample housing member 102, e.g., by using one or more annular spacers. Further, in such embodiments, a target sample can be added to the inside of the annular volume between the outside wall of the pH sensor containment member 104 and the inside wall of the sample housing member 102. In such embodiments, standard NMR and/or MRI analyses known by those skilled in the art may be performed on this double tube assembly. In embodiments, when NMR analyses are applied, the resulting proton NMR signals that emanated from the target sample 108 and the pH sensor 106 may be recorded simultaneously and synchronously by the NMR spectrometer and can be inextricably comingled in the raw data structure, the free induction decay (FID). In such embodiments, a fast Fourier transform (FFT) protocol may be applied to the FID to generate a proton NMR spectrum of the target sample 108 and the pH sensor 106.

In embodiments, in order to generate pH information, a calibration curve can be utilized. In such embodiments, the calibration curve can be composed of a plot of independently, electronically measured pH versus the corresponding NMR parameter (e.g., peak intensity, peak integral, peak chemical shift, spin-lattice relation, spin-spin relaxation). Further in such embodiments, a mathematically-defined curve specific to each sensor molecule is constructed. For example, for a peak intensity NMR parameter measurement, one could select a peak in the $^1$H NMR spectrum of the pH-active molecule, measure and map the peak intensity as a function of independently, electronically-measured pH, use a mathematical function to fit the data, and use the mathematical correlation function to calculate the pH from the $^1$H NMR peak intensity of the pH sensor molecule, and correct pH for temperature variation.

In embodiments utilizing a chemical shift NMR parameter measurement, one could select a peak in the $^1$H NMR spectrum of the pH-active molecule, select another peak from an additionally incorporated nucleus (e.g., $^2$D, $^{13}$C, $^{19}$F, $^{15}$N) as a chemical shift reference observed in a second NMR probe channel, measure and map the relative peak chemical shift, which corresponds to the chemical shift difference from an NMR peak observed in the second NMR probe channel (used a chemical shift reference), as a function of independently, electronically-measured pH, use a mathematical function to fit the data, and use the mathematical correlation function to calculate the pH from the $^1$H NMR peak chemical shift of the pH sensor molecule, and correct pH for temperature variation.

In embodiments utilizing a spin-spin NMR parameter measurement, one could select a peak in the $^1$H NMR spectrum of the pH-active molecule, measure and map spin-spin relaxation rate or time constant as a function of independently, electronically-measured pH, use a mathematical function to fit the data, and use the mathematical correlation function to calculate the pH from the $^1$H NMR peak spin-spin relaxation time constant of the pH sensor molecule, and correct pH for temperature variation.

In Situ NMR Thermometer

As discussed above, various embodiments herein describe an in situ thermometer that can be used in an NMR and/or MRI machine. In one or more embodiments, a device for monitoring actual temperature of a sample in situ with a temperature imprimatur encoded onto the NMR spectrum for accurately determining the thermal properties of the target sample is described. The in situ NMR thermometer described herein is capable of measuring the temperature of an NMR sample in situ and is simple to implement and that encodes and affixes an imprimatur of the measured value of the temperature in the NMR spectrum, affording inseparability of the temperature and the NMR data and incipient integrity of same.

In certain embodiments, the temperature measuring device may include one or more capillary tubes containing a reference material, where such tube(s) is/are centrally or spatially arranged in a sample tube (for solution sample) or a rotor (for solid sample). Any or all tubes may be sealed or unsealed. In embodiments, as discussed below, one or more of the capillary tubes may be sealed using a flame or plasma arc.

Figure 2:
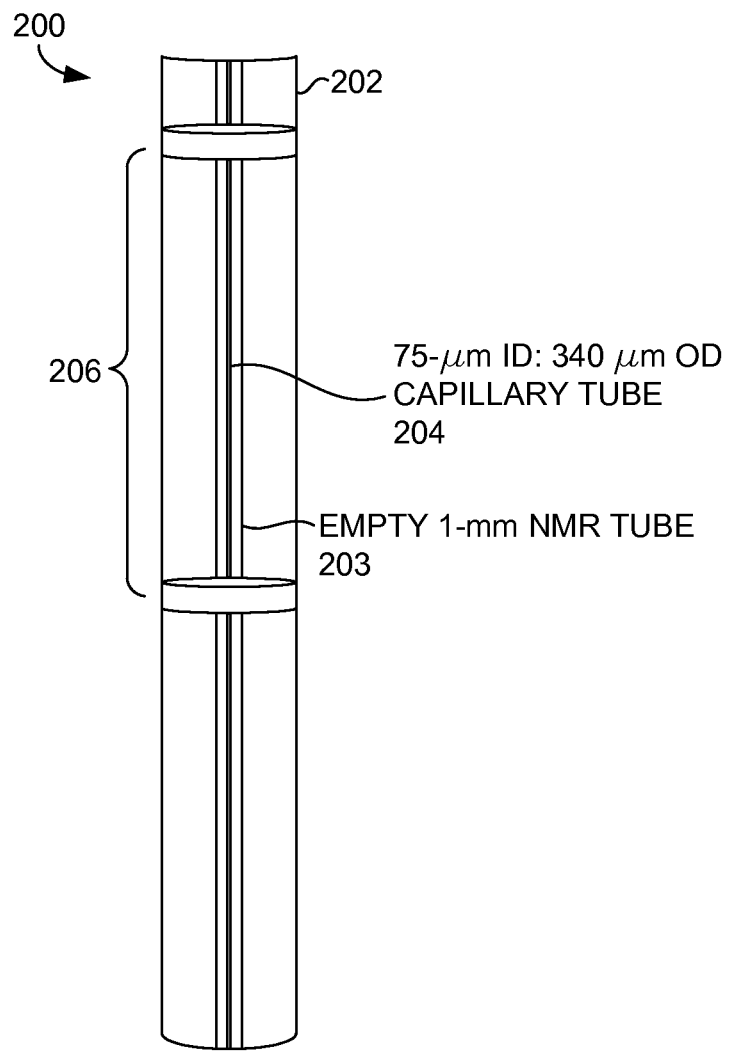
FIG. 2 depicts an in situ NMR thermometer, according to one embodiment described herein.

FIG. 2 shows one embodiment of a temperature measuring device 200. The temperature measuring device 200 can include an NMR tube 202, e.g., a 5 mm coaxial sample 400 MHz J-Young tube, with a smaller inner NMR tube 203, e.g., a conventional 1 mm NMR tube positioned inside of the NMR tube 202. In the temperature measuring device 200 of FIG. 2, a capillary tube 204 can be positioned inside the smaller inner NMR tube 203. The smaller inner NMR tube 203 and/or the capillary tube 204 can be secured inside the NMR tube 202, e.g., by annular spacers 206. In embodiments, the smaller inner NMR tube 203 is empty besides the inserted capillary tube 204, while the NMR tube 202 contains the target sample.

The capillary tube 204 may be configured to house a reference material for the measurement of temperature. In embodiments, the capillary tube 204 can be about 152 mm in length. In one embodiment, the capillary tube 204 can have an outer diameter of at least about 100 micrometers, about 200 micrometers, or about 300 micrometers, and/or an outer diameter of less than about 600 micrometers, 500 micrometers, or 400 micrometers. In certain embodiments, the capillary tube 204 can have an outer diameter of about 340 micrometers. In the same or alternative embodiments, the capillary tube 704 can have an internal diameter of at least about 2 micrometers, about 5 micrometers, about 10 micrometers, about 20 micrometers, about 30 micrometers, 40 micrometers, or 50 micrometers, and/or an internal diameter of less than about 150 micrometers, 125 micrometers, or 100 micrometers. In one embodiment, the capillary tube 204 can have an internal diameter of about 75 micrometers.

In various embodiments, the capillary tube 204 can have an outer diameter that is at least about 2 times larger than the internal diameter, 3 times larger, or 4 times larger. In the same or alternative embodiments, the capillary tube can have an internal diameter that is less than about 75%, about 50%, about 30%, about 20% about 10%, about 5%, or 1% of the outer diameter of the capillary tube 704.

In various embodiments, the smaller inner NMR tube 202 can be about 203 mm in length and about an 0.8 mm internal diameter. In the same or alternative embodiments, the NMR tube 202 can be about 178 mm in length and about a 4.2 mm internal diameter.

As discussed below, in certain embodiments, it may be beneficial to seal the capillary tube 204 so that the reference sample is sealed off from the target sample in the NMR tube 202.

As seen in FIG. 2, the temperature sensor device 200 only includes one reference capillary tube 204, and in this embodiment the capillary tube 204 is centrally located. In alternative embodiments, when more than one reference capillary tube is utilized in the NMR tube 202, these capillary tubes may be spatially arranged, e.g., to measure temperature gradients that may span the target sample.

In various embodiments, a temperature sensor device for use with a solid sample is disclosed. In such embodiments, an external in situ capillary NMR thermometer device for a solid sample can include a capillary tube of a desired length with the reference material (such as ethylene glycol) centrally embedded in the sample contained in a Magic Angle Spinning (MAS) rotor. Such a device is described further below with respect to FIG. 3.

In one or more embodiments, an external in situ capillary NMR thermometer device for a solid sample may include multiple capillary tubes of a desired length with the reference material. In such embodiments, the capillary tubes may be spatially disposed within the sample to monitor spatial variations in sample characteristics, such as the variation of temperature at various locations in the sample contained in the cylindrical rotor.

Figure 3:
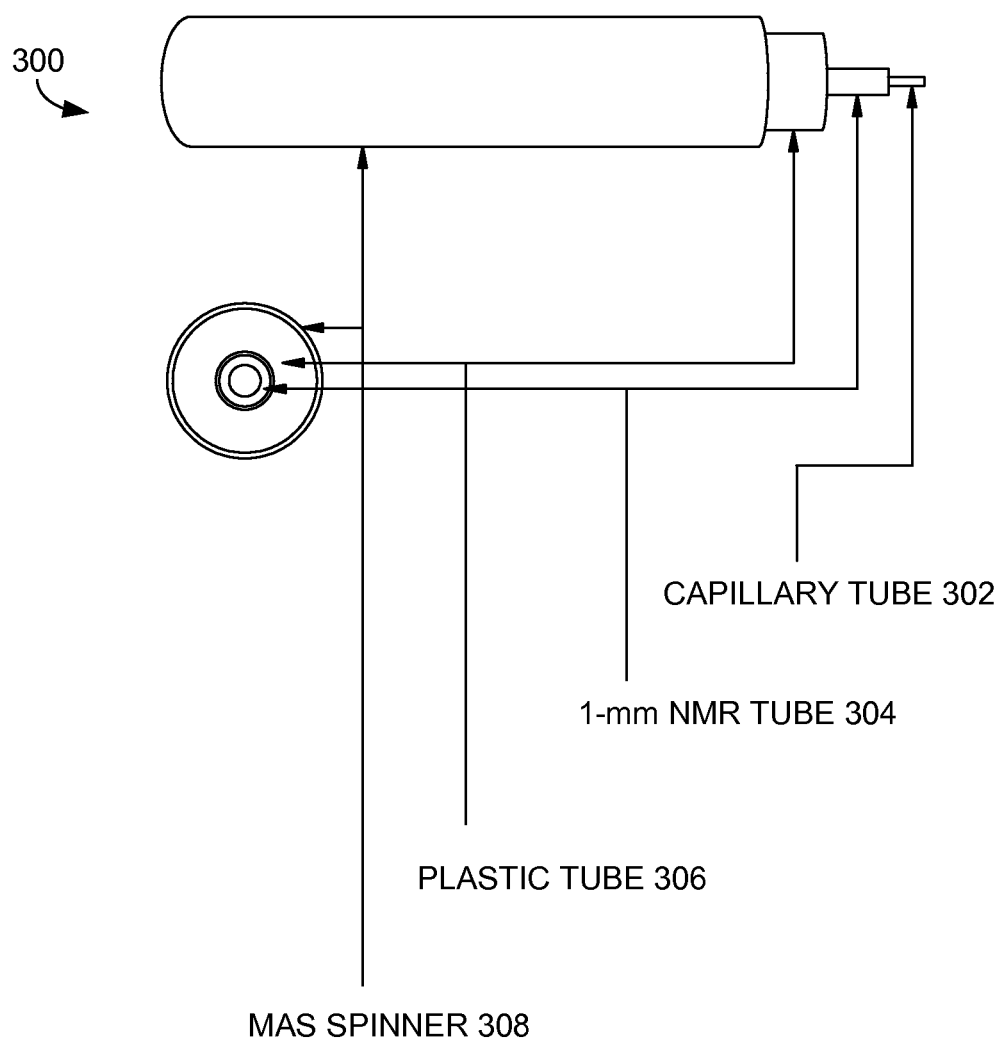
FIG. 3 depicts another in situ NMR thermometer, according to one embodiment described herein.

FIG. 3 depicts a temperature sensor device 300 for in situ temperature measuring for solid state NMR. As shown in FIG. 3, the temperature sensor device 300 can include a sealed capillary tube 302 with a reference material centrally placed in the sample (e.g., a pressed powder) contained in the Magic Angle Spinning (MAS) rotor 308. In the embodiment depicted in FIG. 3, the capillary tube 302 is positioned inside of a 1 mm NMR tube 304, which is positioned inside of a plastic tube 306, which is positioned inside of the MAS rotor. In embodiments, the 1 mm NMR tube 304 and the plastic tube 306 are used to center with capillary tube 302 when no target sample or a minimal amount of target sample used in the MAS rotor.

In embodiments, that do not require a NMR tube 304 and/or a plastic tube 306, the temperature sensor device 300 may only include the MAS rotor 308 and the capillary tube 302. In such embodiments, a powder sample can be packed inside the MAS rotor 308. Further, in such embodiments, a drill bit or similar device can be used to bore a hole in the sample centrally located in the MAS rotor 308. In addition, in such embodiments, a sealed capillary tube 302 with reference material is placed in the bored hole. Further, a packing tool having an end in the shape of a tube is used to pack the powder sample tightly around the sealed capillary tube 302.

As discussed above, a capillary tube, e.g., the capillary tube 204 and/or the capillary tube 302, can include a reference material for the in situ measurement of pH. The reference material may be one or more of compounds that have one or more NMR peaks that change chemical shift as a function of temperature. The reference material may be a liquid, solid, and/or gaseous material. In one or more embodiments, a liquid reference material may include one or more of ethylene glycol, methanol, ethanol, NaF in $D_2O$, alcohols, glycols, polyethylene glycols. In various embodiments, solid reference materials may include one or more of lead nitrate, cobalt complexes, etc. In certain embodiments, gaseous reference materials include one or more of methane, xenon, mixture of xenon with oxygen, $CF_4$, $CF_2(OF)_2$, $CF_3C_{F3}$, $CF_2CF_2$.

The capillary tubes 204 and 302, may in various embodiments, may include one or more materials that include glass, quartz, Peek, Torlon, Teflon, *Arum*, and other polymers and ceramic materials. In one embodiment, the capillary tubes 204 and 302 do not include a metal material.

Systems and Methods for Sealing a Capillary Tube for an In Situ NMR Thermometer

As discussed above, one or more capillary tubes that house the temperature reference material for an in situ NMR thermometer may be sealed. It is appreciated that the sealing system and methods described herein can be useful for use with other devices, in addition to an in situ NMR thermometer, such as devices requiring sealed capillaries to survive at high temperatures and pressures in harsh environments.

In embodiments, a glass seal may be used at one or both ends of the capillary tube. In certain embodiments, an Optical Fiber Arc Fusion Splicer may be used to generate such a glass seal.

In certain embodiments, a method generally comprises the steps of i) selecting a suitable capillary tube with desired length, internal diameter, and outer diameter for a particular application, ii) filling said capillary tube with preselected (solid, liquid, or gas) reference material, iii) sealing a first end of such capillary tube, and iv) sealing a second end of capillary tube, whereas sealing a capillary tube may involve means of glue, epoxy, plugs, etc., or an electric arc fusion approach utilizing an Optical Fiber Arc Fusion Splicer.

According to an exemplary embodiment of the invention, the inventive method for sealing a capillary tube comprises the following steps:

(1) Use epoxy to seal a needle to one end of a desired capillary tube.
(2) Use a knife to scrape off the coating (about 1 cm long) from the other end of the capillary tube.
(3) Fill a sample solution into a syringe.
(4) Connect the needle to the syringe.
(5) Push the solution though the capillary tube until 2 to 3 drops comes out of the open end of the capillary tube.
(6) Wipe the end of the capillary tube.
(7) Place the open end of the capillary tube in the arc fusion splicer.
(8) Check the fusion splicer display screen to find the gas/liquid interface.
(9) Push the syringe plunger in order to keep the gas liquid interface about 0.1 mm from the open end of capillary tube.
(10) Apply the arc with a constant 0.05N force on the syringe plunger.
(11) Take the sealed capillary tube out of the arc fusion splicer.
(12) Choose the length of the capillary tube that you want, and cut off the portion that is affixed to the syringe needle.
(13) Use a knife to scrape off the coating (about 1 cm long) from the open end of the capillary tube.
(14) Place the open end of the capillary tube in the arc fusion splicer, and then apply the arc.
(15) Use a microscope to check the sealed ends of the capillary tube.

Figure 4:
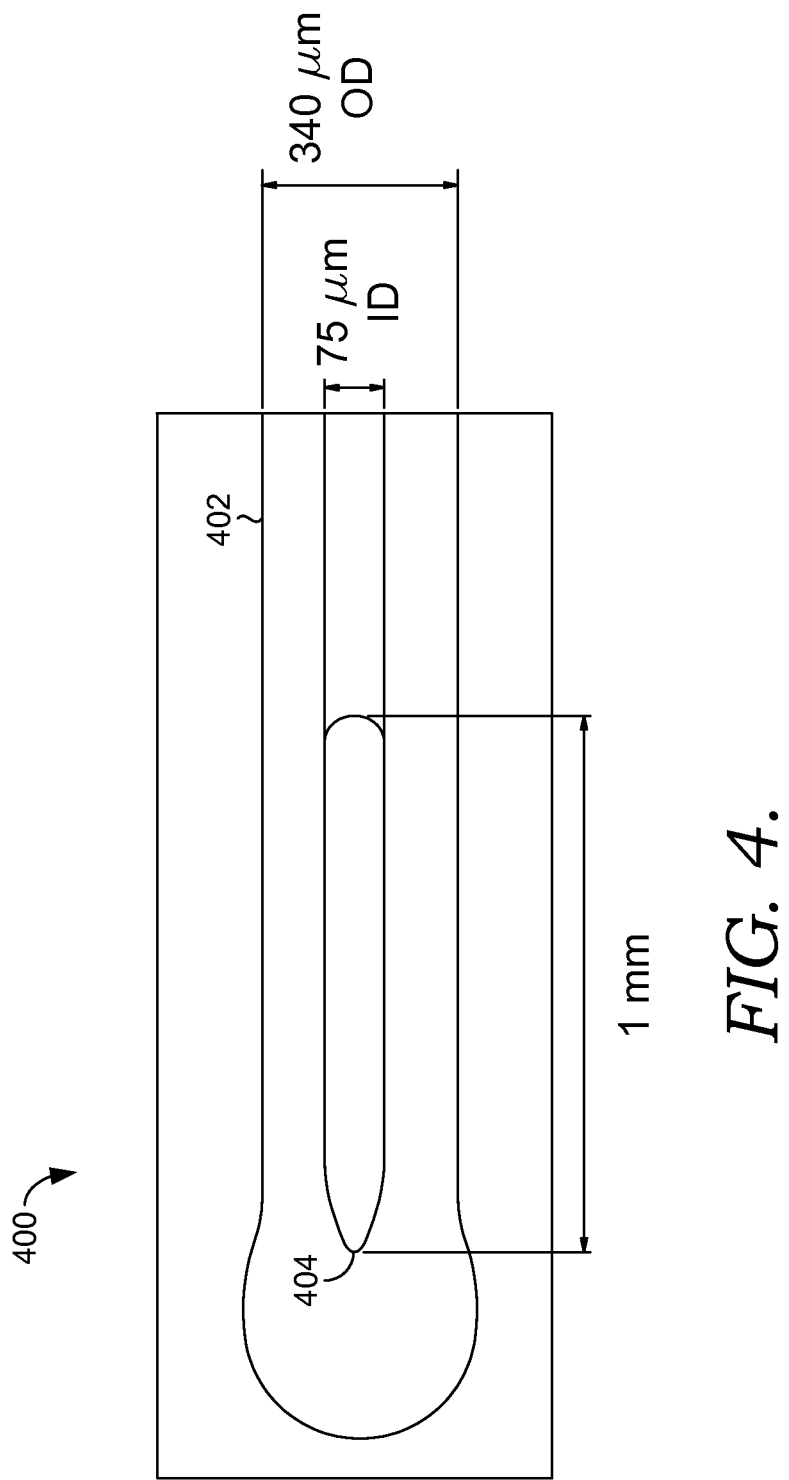
FIG. 4 depicts a schematic view of a sealed capillary tube end, according to one embodiment described herein.

A schematic representation 400 of a sealed capillary tube 402 is depicted in FIG. 4. The capillary tube 402 includes a end 404 that is sealed by glass or other material from the capillary tube 402. In embodiments, when using an Optical Fiber Arc Fusion Splicer to seal the end 404 of a capillary tube 402, it may be beneficial to maintain a liquid, gas, or solid reference material inside the capillary tube 402 at least about 1 mm away from the end 404 of the tube so as to not inadvertently heat up the reference material. In various embodiments, the reference material should be kept at least about 0.75 mm away from the end 404 being sealed by the Optical Fiber Arc Fusion Splicer, or at least about 0.5 mm, or at least about 0.3 mm, or at least about 0.1 mm.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

EXAMPLES

The concepts discussed herein will be further described in the following examples, which do not limit the scope of various embodiments described in the claims.

Example 1: Phenolphthalein as a pH Sensor for In Situ pH Measurements

In this example, the in situ pH measuring device included a standard NMR tube as the sample housing member where a sample (in the sample solution) was contained and a central capillary tube made of VYCOR® glass as the containment member was used where the pH sensor was contained. In this example, phenolphthalein was utilized as the pH sensor.

Specifically, the exemplary embodiment comprised a commercial 5 mm outer diameter, 17 cm long borosilicate glass NMR tube as the sample housing member and a 1 mm outer diameter, 17 cm long VYCOR® porous capillary tube as the containment member for the pH sensor molecule phenolphthalein. The size of a sequestered phenolphthalein molecule is approximately seven Angstroms; the VYCOR® porous capillary pH sensor tube is selected for pore sizes that are smaller than the phenolphthalein molecule, but large enough (about two Angstroms in diameter) to allow unobstructed passage of hydronium and hydroxide ions. During the NMR testing, the VYCOR® porous capillary tube was filled to a height of approximately 7 cm from the bottom with a 0.001 molar aqueous solution of phenolphthalein, and placed approximately concentrically within the 5 mm glass NMR tube. The target sample, an aqueous acid solution, analyzed by NMR or MRI methods was placed inside the annular volume between the outside wall of the containment tube and the inside wall of the 5 mm glass NMR tube and filled to a level of approximately 7 cm from the bottom of both tubes. Standard NMR and MRI analyses were performed on the entire concentric tube assembly. The resulting proton NMR signals that emanated from the target sample solution and the phenolphthalein pH sensor molecule were recorded simultaneously and synchronously by the NMR spectrometer and were inextricably comingled in the raw data structure, also known as the free induction decay (FID). A fast Fourier transform (FFT) was applied to the FID data to generate a proton NMR spectrum of the target sample solution and the phenolphthalein pH sensor molecule.

To generate the NMR spectra, 3 microliters of a 0.01 molar NaOH solution was added to the NMR tube and the proton NMR spectrum was recorded. This was repeated (ten times) until a total of 30 microliters had been added. Additionally, an electronic pH meter was utilized to test the pH of each different target sample solution that was in the NMR tube.

Figure 5A:
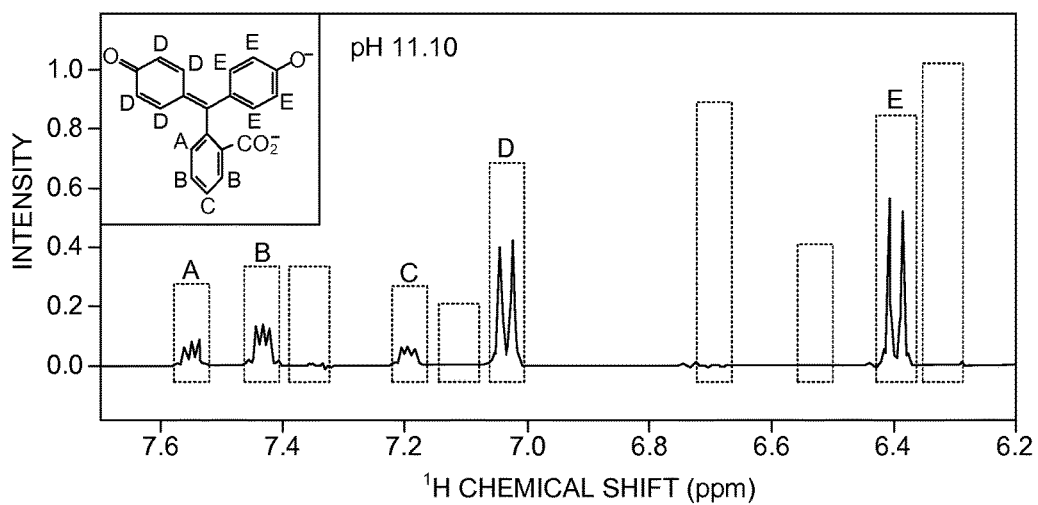
FIG. 5A is a graph of proton NMR peaks of phenolphthalein at a pH of 11.1 as described in Example 1, according to one embodiment described herein.
Figure 5B:
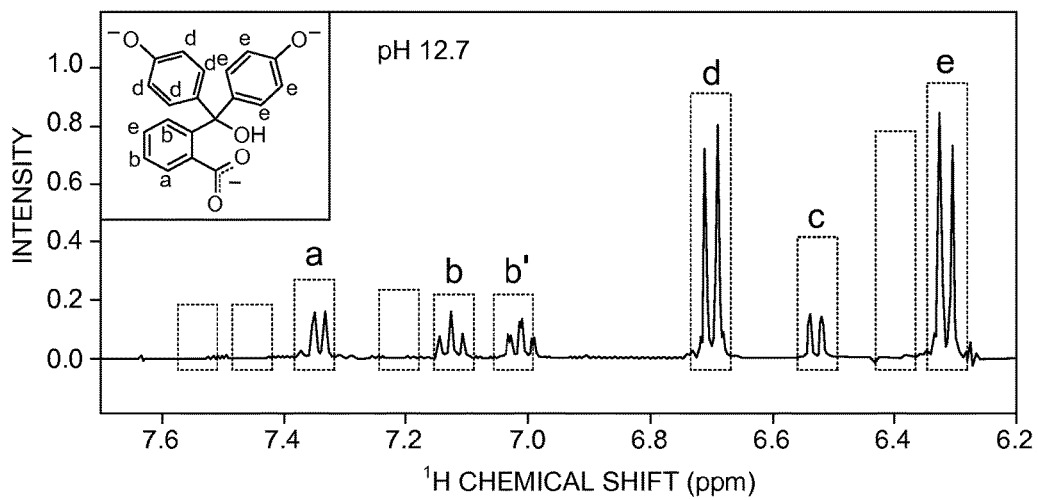
FIG. 5B is a graph of proton NMR peaks of phenolphthalein at a pH of 12.7 as described in Example 1, according to one embodiment described herein.

The phenolphthalein molecule is known to exist exists in two different structural forms depending on the pH of the solution. FIGS. 5A and 5B illustrate the pH induced spectral changes of the exemplary pH sensor (phenolphthalein) at two different pH values. One form of the pH sensor probe molecule is shown in FIG. 5A for pH 11.1; a different structural form of the pH sensor probe molecule is shown in FIG. 5B for pH 12.7.

A comparison of FIG. 5A and FIG. 5B reveals two sets of proton NMR peaks for the pH sensor probe molecule phenolphthalein when it exists in two different forms, under conditions of different pH. The proton resonances for each group of chemically equivalent protons are contained in eleven distinct boxes and labeled with capital letters (FIG. 5A) or lower case letters (FIG. 5B) according to each of the respective structures depicted in FIGS. 5A and 5B. At pH 11.1 only one form of phenolphthalein molecule is present, while at pH 12.7 only the other form is present. These changes in peak intensities of the 1H NMR spectrum of the phenolphthalein pH sensor were correlated with the electronically-measured pH values that ranged from pH 11.1 to 12.7.

Figure 5C:
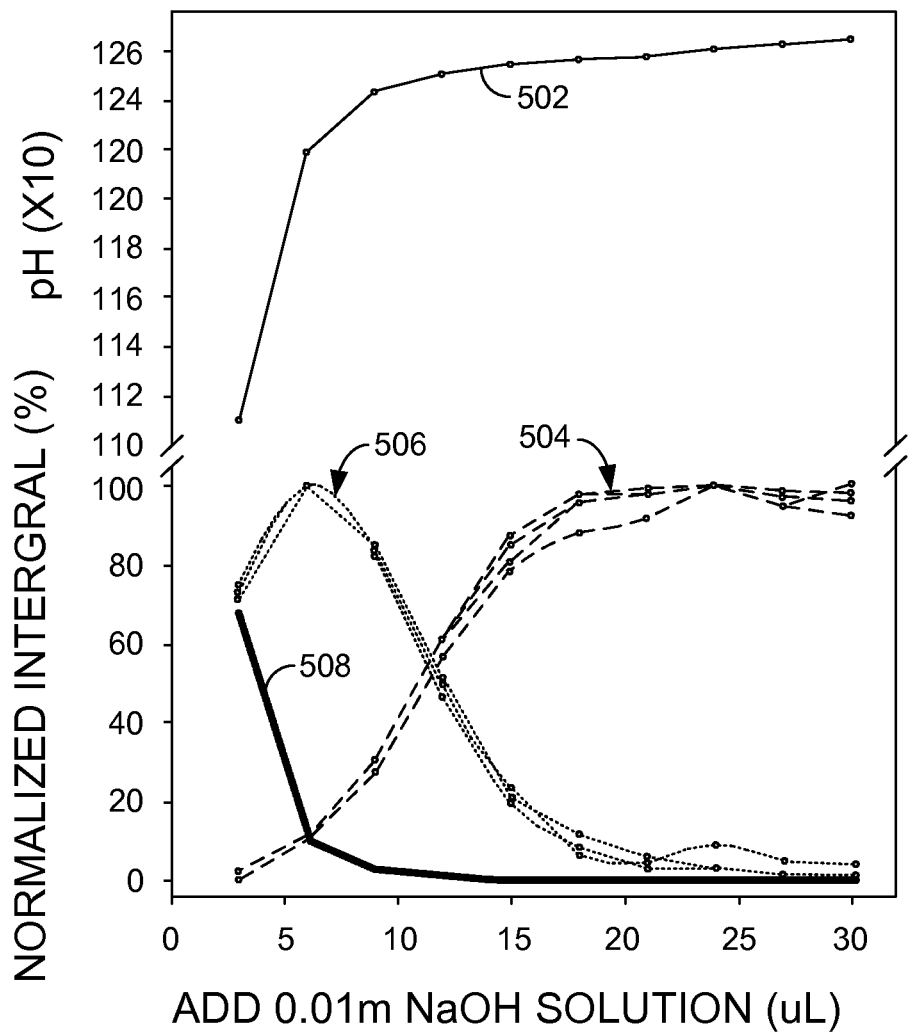
FIG. 5C is a graph containing multiple plots of peak integrals, ratios of peak integrals and pH values for a phenolphthalein solution as described in Example 1, according to one embodiment described herein.

Measurements of the intensities from both sets of proton NMR peaks from FIGS. 5A and 5B are plotted in FIG. 5C, and were used in conjunction with a pH calibration curve shown in the top portion of FIG. 5C to determine the pH of the target sample solution. FIG. 5C is a graph containing multiple plots of peak integrals and pH values for a solution of 7.7 mg of phenolphthalein in 600 microliters of $D_2O$ as a function of 3 microliter additions of 0.01 molar NaOH. The group of lines 506 are plots of normalized proton NMR peak integrals for the phenolphthalein structure shown in FIG. 5A as a function of 3 microliter additions of 0.01 molar NaOH. The group of lines 504 are plots of normalized proton NMR peak integrals for the phenolphthalein structure shown in FIG. 5B as a function of 3 microliter additions of 0.01 molar NaOH. The line 508 is a plot of the ratio of intensities of corresponding selected peaks from the proton NMR spectra from FIGS. 5A and 5B. The line 502 is a plot of the measured pH using an electronic pH meter. The proton NMR spectra for phenolphthalein solutions at pH values between 11.1 and 12.7 revealed the proton resonances for both structures in varying proportions.

The absolute intensity of each peak in the spectrum was measured by integration over the signal. Further, a mathematical correlation function was used to calculate the pH from a 1H NMR peak intensity of phenolphthalein pH sensor molecule. The pH was corrected for temperature variation by repeating the previous steps for each temperature setting for a series of temperatures that covered the temperature range of interest for investigations of the target sample solution. This example provides the paradigm for in situ monitoring of pH by $^1H$ NMR spectroscopy via peak intensities with the advantage of a spectral pH imprimatur.

Example 2: NaF as a pH Sensor for In Situ pH Measurements

In this example, the pH-induced spectral changes of another exemplary pH sensor, sodium fluoride (NaF), was categorized by Fluorine-19 NMR chemical shift. The in situ pH measuring device utilized in this example includes a commercial 5 mm outer diameter, 17 cm long borosilicate glass NMR tube as the sample housing member and a 1 mm outer diameter, 17 cm-long cracked-tip capillary pH sensor tube as the containment member for the pH sensor molecule, NaF. The cracked-tip capillary tube was prepared by heating the bottom (closed end) of the tube and rapidly quenching the hot glass in cold water, causing a crack in the glass. The size of a sequestered solvated NaF molecule is approximately three Angstroms, and thus, the cracked-tip capillary pH sensor tube was selected for crack sizes that are smaller than the solvated NaF molecule, but large enough (about two Angstroms in diameter) to allow unobstructed passage of hydronium and hydroxide ions. The cracked-tip capillary tube was filled to a height of approximately 7 cm from the bottom with a 0.001 molar aqueous solution of NaF, and placed approximately concentrically within the 5 mm glass NMR tube.

The target sample material analyte molecule (1,1,1,2,2-pentafluorododecan-3-ol) was analyzed by NMR or MRI methods by placing an aqueous solution of it inside the annular volume between the outside wall of the cracked-tip pH sensor tube and the inside wall of the 5 mm glass NMR tube, filled to a level of approximately 7 cm from the bottom of both tubes. Standard 19F NMR and MRI analyses were performed on the concentric tube assembly.

The resulting fluorine-19 NMR signals that emanated from the sample material (1,1,1,2,2-pentafluorododecan-3-ol) and the NaF pH sensor probe molecule were recorded simultaneously and synchronously by the NMR spectrometer and were inextricably comingled in the raw data, also known as the free induction decay (FID). A fast Fourier transform (FFT) was applied to the FID to generate an 19F NMR spectrum of the target sample material analyte molecule (1,1,1,2,2-pentafluorododecan-3-ol) and the sodium fluoride pH sensor probe molecule.

Figure 6:
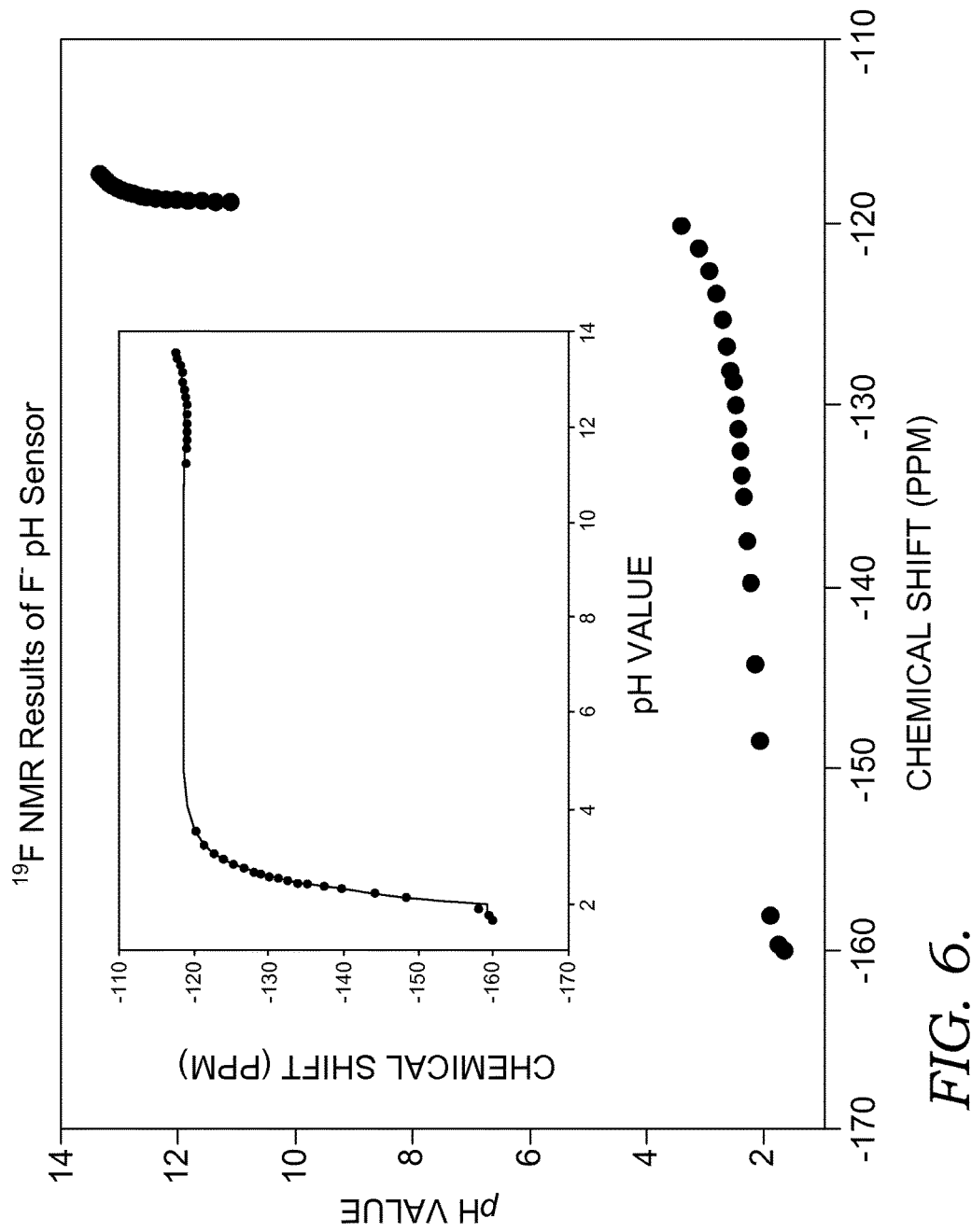
FIG. 6 is a plot of $^{19}F$ pH as a function of chemical shift of a solution of NaF in $D_2O$ as described in Example 2, according to one embodiment described herein.

FIG. 6 depicts a plot of pH as a function of the 19F chemical shift for an acidic and basic solution of 7 milligrams of NaF in 600 microliters of $D_2O$. The acidic solution was made using 2.5 microliter additions of 0.001 molar HCl from pH 1.7 to pH 3.5. The basic solution was made using 2.5 microliter additions of 0.005 molar NaOH from pH 11.0 to pH 13.5. The inset on the plot shows 19F chemical shift as a function of pH and the equation that was used to fit the data points. The change of NaF chemical shifts from pH 1.7 to pH 4.5 varied greatly. In that range, a change in one or more decimal positions for the pH value was observed, e.g., a chemical shift of NaF between pH 4.40 and 4.41 was observed, as opposed to 4.4 to 4.5.

NMR spectra for the NaF pH sensor and a target molecule were obtained by preparing the NMR tube using 600 microliters of $D_2O$, 7 mg of NaF, and 3 microliters of the target molecule, 1,1,1,2,2-pentafluorododecan-3-ol. 2.5 microliters of 0.001 molar HCl solution was added to the NMR tube and the 19F NMR spectrum was recorded. This was repeated until a total of 42.5 microliters of HCl had been added to the tube, then two additions of 10 microliters of the HCl solution were performed, followed by three 50 microliter additions of the HCl solution until a total of 212.5 microliters of the HCl solution had been added. After each HCl addition, the target sample in the NMR tube was measured with an electronic pH meter.

Another NMR tube was prepared using 600 microliters of $D_2O$, 7 mg of NaF, and 3 microliters of 1,1,1,2,2-pentafluorododecan-3-ol. 2.5 microliters of a 0.005 molar NaOH solution was added to the NMR tube and the 19F NMR spectrum was recorded. This was repeated until a total of 20 microliters was added, then 10 microliter portions of the NaOH solution was added until a total of 80 microliters of NaOH had been added to the NMR tube, followed by addition of 100 microliter portions of the NaOH solution until a total of 1080 microliters of the NaOH solution had been added to the NMR tube. After each NaOH addition, the target sample in the NMR tube was measured with an electronic pH meter.

Figure 7A:
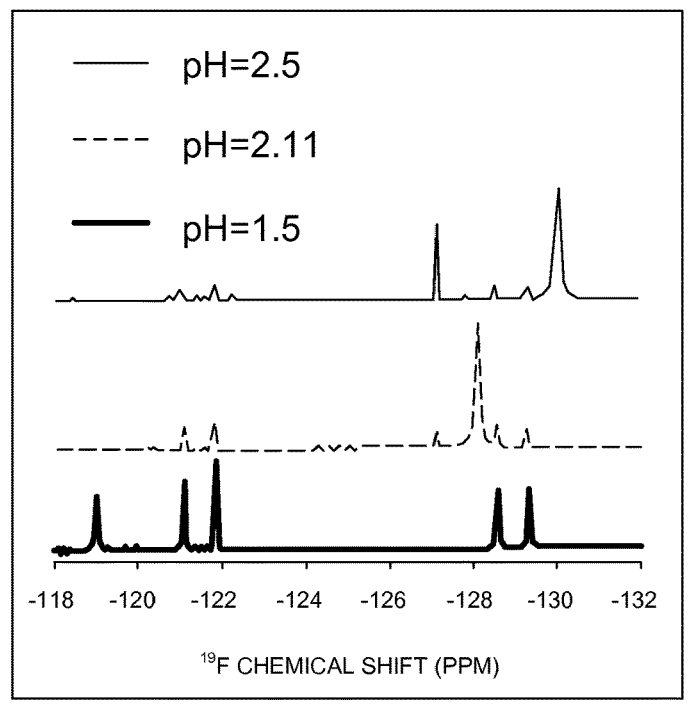
FIGS. 7A and 7B are $^{19}F$ NMR spectra of pH test molecule 1,1,1,2,2-pentafluorododecan-3-ol with NMR pH sensor NaF for two ranges of pH as described in Example 2, according to one embodiment described herein.

FIG. 7A depicts the 19F NMR spectrum of NaF for a multitude of different structural forms depending on the pH of the acidic target solution. For example, one form of the pH sensor probe molecule is represented by an NMR peak at approximately −119 ppm for pH 1.5; a different structural form of the pH sensor molecule is depicted by an NMR peak at approximately −128 ppm for pH 2.11. FIG. 7A also shows the 19F NMR spectrum of the pH sensor probe molecule at approximately −130.5 ppm for pH 2.5.

Figure 7B:
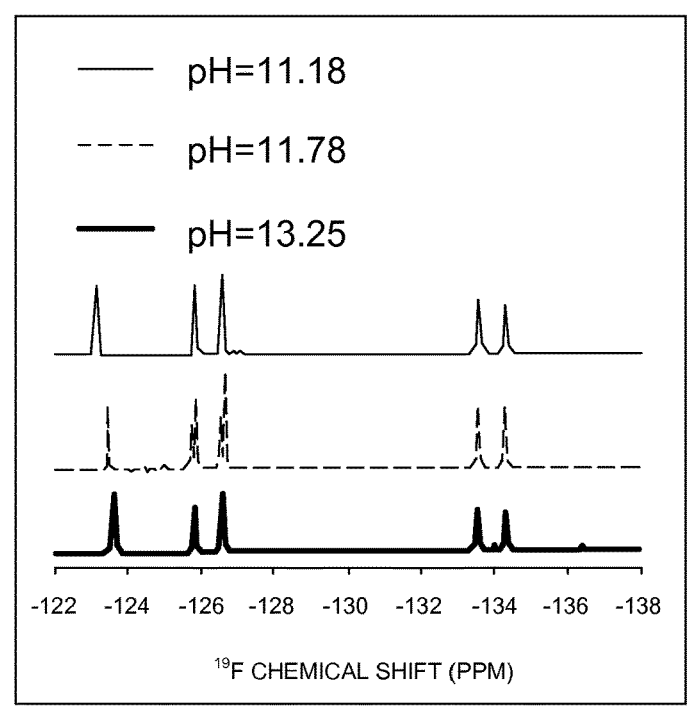

FIG. 7B depicts the 19F NMR spectrum of NaF for a multitude of different structural forms depending on the pH of the basic target solution. For example, one form of the pH sensor probe molecule is represented by an NMR peak at approximately −123 ppm for pH 11.18; a different structural form of the pH sensor molecule is depicted by an NMR peak at approximately −123.5 ppm for pH 11.78. FIG. 7B also shows the fluorine NMR spectrum of the pH sensor probe molecule at approximately −123.75 ppm for pH=13.25.

FIGS. 7A and 7B also include the 19F NMR spectra of the target sample material analyte molecule (1,1,1,2,2-pentafluorododecan-3-ol) for multiple pH environments. The 19F NMR spectrum of the target sample material analyte in FIG. 7A is revealed by a set of five NMR peaks at approximately −121, −122, −127, −128.5, and −129.5 ppm. The 19F chemical shifts have shifted to the right for different pH values and the target sample peaks have changed. The 19F NMR spectrum of the target sample material analyte molecule (1,1,1,2,2-pentafluorododecan-3-ol) in FIG. 7B is revealed by a set of four NMR peaks at approximately −126, −126.5, −133.5, and −134.5 ppm. The 19F chemical shifts have shifted to the left for different pH values and the target sample peaks have not changed.

Figure 8:
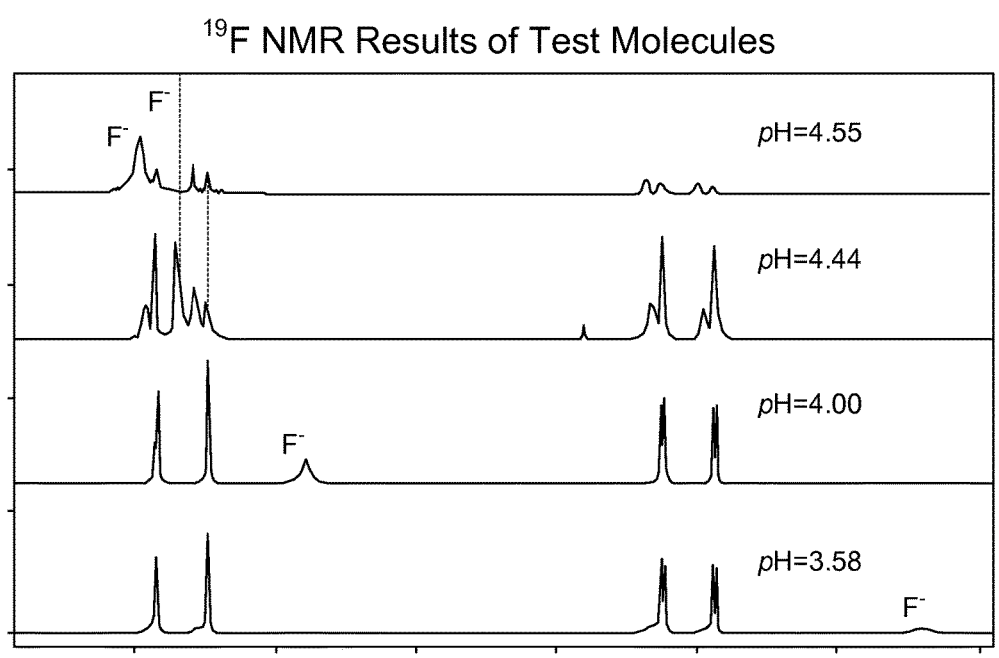
FIG. 8 is $^{19}F$ NMR spectra of pH test molecule 1,1,1,2,2-pentafluorododecan-3-ol at various pHs as described in Example 2, according to one embodiment described herein.

FIG. 8 depicts the 19F NMR spectra of the target sample material analyte molecule (1,1,1,2,2-pentafluorododecan-3-ol). Peaks changed with NMR pH sensor peak (NaF) for four different pH values. When the pH was 3.58 and 4, the peaks for the target sample analyte did not change much. When the pH was 4.44 and 4.55 the target sample analyte peak changed to indicate two separate molecular species.

Measurements of the 19F chemical shifts for NaF can be used in conjunction with a calibration curve shown in FIG. 6 to determine the pH of the solutions of target sample material analyte molecules. A mathematical correlation function was used to calculate pH from a 19F peak chemical shifts of the NaF pH sensor molecule. The pH was corrected for temperature variation. This example provides the paradigm for in situ monitoring of pH by 19F NMR spectroscopy via chemical shifts with the advantage of a spectral pH imprimatur.

Example 3: Using an In Situ Temperature Sensor to Measure the Activation Energy of the Conformation Change of DPPH External in situ temperature monitoring during NMR test of 2,2-diphenyl-1-picrylhydrazine (DPPH) in CDCl$_3$. The external in situ temperature sensor device was made of a sealed capillary tube (75 um internal diameter, 364 um outer diameter, 6 cm length). The capillary tube was filled with 100% ethylene glycol. The external in situ temperature sensor device was assembled similar to that depicted in FIG. 2. For example, the external in situ temperature sensor device was inserted into a 5-mm NMR tube, which was filled with DPPH solution. The external in situ temperature sensor device monitored the actual temperature of the DPPH sample in situ, and provided a temperature imprimatur. That is, the raw data/NMR spectra of the DPPH also includes the data of the ethylene glycol external in situ temperature sensor.

Figure 9:
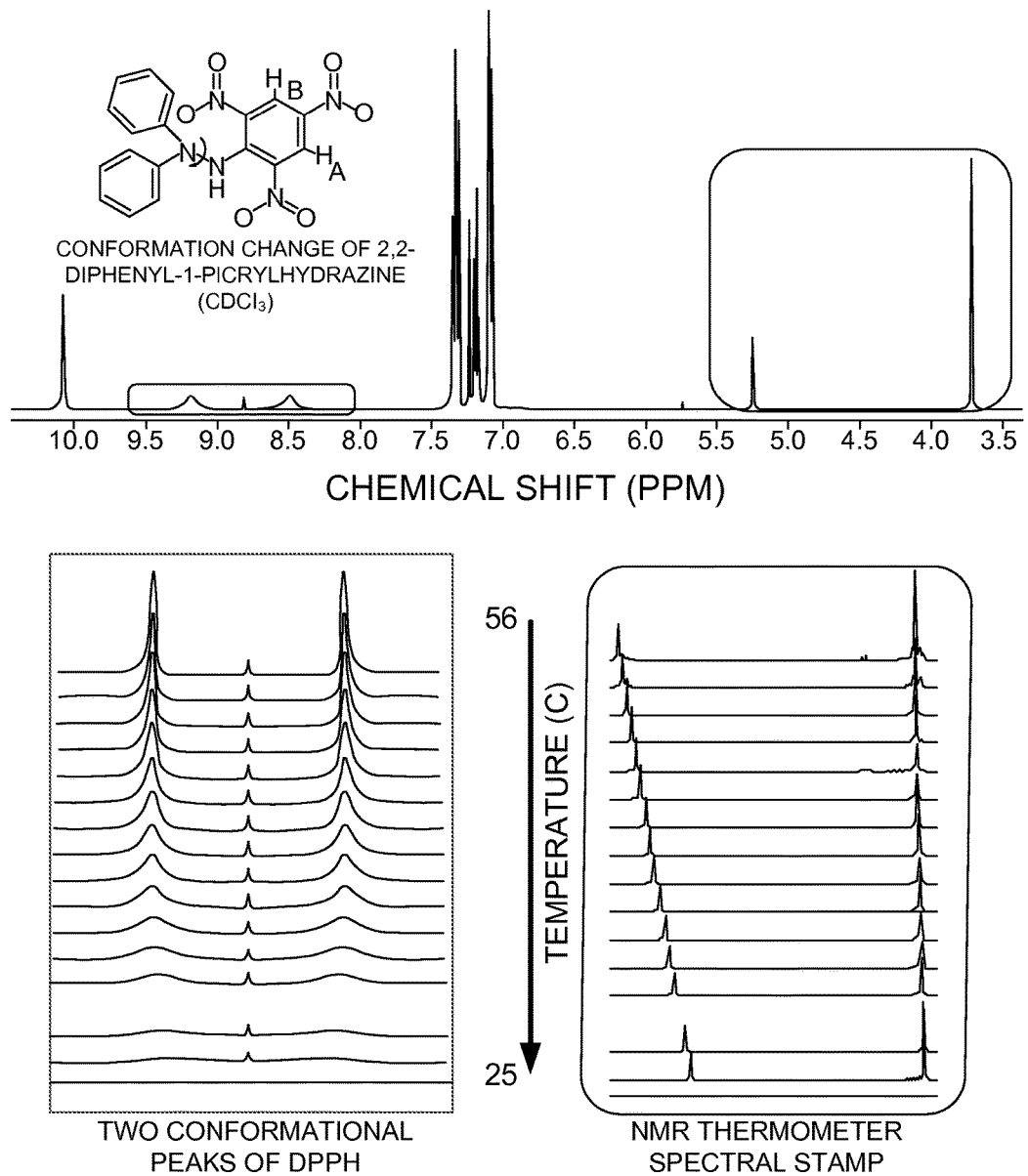
FIG. 9 depicts the NMR spectra of 2,2-diphenyl-1-picrylhydrazine at various temperatures using an in situ temperature sensor as described in Example 3, according to one embodiment described herein.

In this example, NMR spectra were recorded for DPPH sample (and the ethylene glycol external in situ temperature sensor) at temperatures from 25-56° Celsius in 2° Celsius increments. FIG. 9 shows a full exemplary spectrum with the box on the left highlighting to the two conformational peaks of DPPH and the box on the right highlighting the in situ thermometer spectral stamp (of ethylene glycol). Below the full spectrum is the individual spectrum at various temperatures in 2° increments (between 25-56° Celsius). By conducting a one pulse experiment, two peaks were successfully observed to reveal the conformational exchange of DPPH, and the two peaks of ethylene glycol that provided the temperature measurement. This data shows how the conformational change of DPPH correlates with various temperatures of the DPPH, as evidenced by the spreading out of the two prominent spectral peaks in the in situ thermometer containing ethylene glycol.

The proton NMR spectrum of ethylene glycol reference material can be used to determine the actual temperature of the ethylene glycol reference material, and of the DPPH, as they are in the same thermal environment of the in situ thermometer device. For example, a proton NMR spectrum of the ethylene glycol reference material contained in the capillary tube produces two sharp peaks. The separation of the two peaks measured in frequency units of Hz is entered into a standard published temperature calibration formula specific to ethylene glycol. The formula generates a numerical output that is the temperature of the ethylene glycol, capillary tube and surrounding sample.

Figure 10:
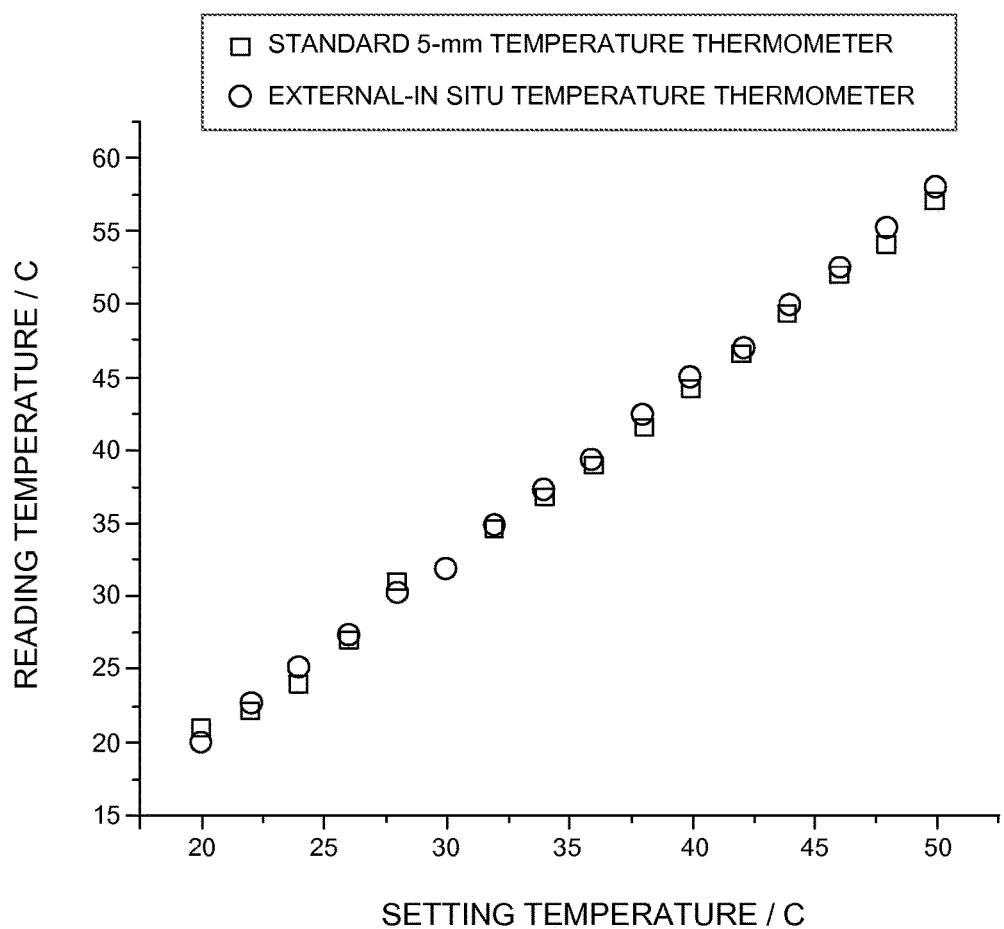
FIG. 10 is a plot of the setting and reading temperatures of ethylene glycol using a commercially available temperature probe and the in situ temperature sensor as described in Example 3, according to one embodiment described herein.

FIG. 10 depicts a graph comparing the temperature determined for the in situ temperature sensor used in this Example 3 with the temperature determined using a commercial NMR thermometer device. As can be seen in FIG. 10, the in situ temperature sensor used in this Example 3 produces similar temperature results as that using a commercial NMR thermometer.

Example 4: In Situ Temperature Monitoring During NMR Test of a Solid Sample

External in situ temperature monitoring during NMR test of a solid sample. The in situ temperature monitoring device was made of a sealed capillary tube (75 micrometer internal diameter, 364 micrometer outer diameter, 1 centimeter length). The capillary tube was filled with 100% ethylene glycol.

The MAS rotor and in situ temperature monitoring device were assembled similar to that described with respect to FIG. 3. For example, the MAS rotor contained a powder target sample illustrated. The plastic tube can be made of a polymer that is the target sample material that is to be analyzed for composition of plasticizer, for example. The 1 mm NMR tube is made of glass and is used as an element to keep the target sample and the NMR thermometer sensor centered so that the rotor will maintain balance during high speed rotation. Any cylindrical element made of a material that does not produce an NMR signal that will interfere with the NMR signals from the target sample is suitable (glass, ceramic tubes, etc.) can be used for this purpose. The MAS rotor itself is made of a ceramic (zirconia) and it does not produce NMR signals that interfere with the NMR signals produced by the target sample material. The arrangement of the target sample material, the cylindrical spacer element, the NMR capillary thermometer should be arranged so as to produce a rotationally-balanced system within the rotor, so cylindrical symmetry is not absolutely necessary. This embodiment has cylindrical symmetry. A cap is placed on the rotor to seal in the contents. The rotor is placed in the MAS probe.

The in situ temperature monitoring device monitored the actual temperature of the sample in situ, and provided a temperature imprimatur. Air jets were used to cause the rotor to spin at from 1-14 kHz in the. A one-pulse experiment during MAS was conducted.

Figure 11:
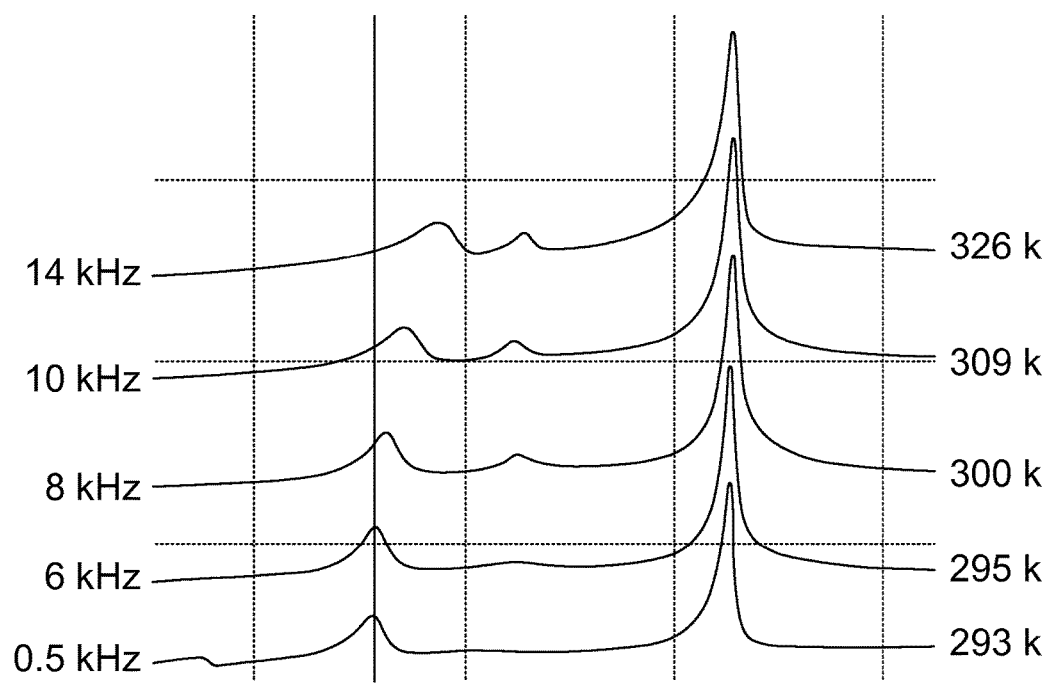
FIG. 11 is NMR spectra of a solid sample using an in situ temperature sensor as described in Example 4, according to one embodiment described herein.
Figure 12:
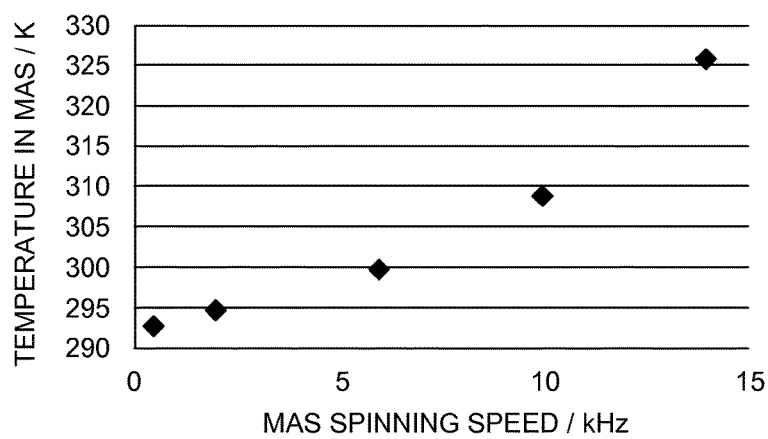
FIG. 12 is a plot of the spinning speed of the MAS rotor and the temperature of the reference material, and a numerical table is also provided for this graph, as described in Example 4, according to one embodiment described herein.

FIG. 11 shows a set of stacked spectra that reveal the temperature as metered by the thermometer and indicated by the difference between left most peak (with the vertical line) and the right most sharper peak as measured in Hz or PPM. This difference is entered into a well-known equation that outputs the temperature at the location of the NMR thermometer sensor. The temperature is indicated at the right. As the rotation speed of the rotor increases, the two peaks come closer together. The equation takes in the separation of the two peaks in Hz or PPM and outputs the temperature of the NMR temperature sensor in Kelvins. The bottom axis of the NMR plots is Hz or PPM. The temperature of the rotor increases with spinning speed as shown in FIG. 12, which is a plot of the temperatures of the NMR thermometer sensor molecule as a function of spinning speed.

What is claimed is:

1. A device for in situ pH monitoring of a sample using Nuclear Magnetic Resonance (NMR) spectroscopy, the device comprising:
    a sample housing member configured to house a target sample;
    at least one pH sensor configured to exhibit an NMR spectral change due to a change in pH value of the target sample; and
    a pH sensor containment member having an interior portion, the pH sensor containment member configured to maintain the at least one pH sensor in the interior portion, where the pH sensor containment member is positioned inside at least a portion of the sample housing member, wherein at least a portion of the pH sensor containment member comprises one or more pores, wherein the one or more pores are configured to allow bidirectional diffusion of hydronium cations and hydroxide anions while maintaining the at least one pH sensor in the interior portion and while precluding direct interaction of the at least one pH sensor and the target sample.

2. The device of claim 1, wherein the at least one pH sensor exhibits a peak volume change induced by pH value changes in a sample environment.

3. The device of claim 1, wherein the at least one pH sensor exhibits a peak chemical shift induced by pH value changes in a sample environment.

4. The device of claim 1, wherein the pH sample containment member is any high surface area fiber or thin rod that immobilizes pH sensor molecules by entrapment or by physical tethers, the high surface area fiber or the thin rod allowing for a bidirectional transport of one or more of the hydronium cations or the hydroxide anions while impeding a transport of a target sample molecule and a pH sensor molecule.

5. The device of claim 1, wherein the at least one pH sensor is configured to produced NMR signals from nuclei other than nuclei that produce NMR spectra of the target sample.

6. The device of claim 1, wherein the pH sensor containment member is comprised of glass.

7. A method for measuring a pH of a sample in situ using Nuclear Magnetic Resonance (NMR) spectroscopy, the method comprising:
    providing an in situ NMR pH measurement device, the device comprising:
    (1) a sample housing member configured to house a target sample,
    (2) at least one pH sensor configured to exhibit an NMR spectral change due to a change in pH value of the target sample, and
    (3) a pH sensor containment member having an interior portion, the pH sensor containment member configured to house the at least one pH sensor, wherein at least a portion of the pH sensor containment member comprises one or more pores, wherein the one or more pores are configured to allow bidirectional diffusion of hydronium cations and hydroxide anions while maintaining the at least one pH sensor in the interior portion and while precluding direct interaction of the at least one pH sensor and the target sample;
    adding the target sample to the sample housing member;
    obtaining one or more NMR spectra; and determining the pH of at least a portion of the target sample.

8. The method of claim 7, further comprising identifying a type of pH sensor to use in the in situ NMR pH measurement device.

9. The method of claim 7, wherein the at least one pH sensor is configured to produced NMR signals from nuclei other than nuclei that produce NMR spectra of the target sample.

10. The method of claim 7, wherein the pH sensor containment member is comprised of glass.

* * * * *